(12) United States Patent
Unkefer et al.

(10) Patent No.: US 9,446,992 B2
(45) Date of Patent: Sep. 20, 2016

(54) COMPOUNDS AND METHODS FOR IMPROVING PLANT PERFORMANCE

(71) Applicants: Los Alamos National Security, LLC, Los Alamos, NM (US); University of Maine System Board of Trustees, Bangor, ME (US)

(72) Inventors: Pat J. Unkefer, Los Alamos, NM (US); Thomas Joseph Knight, Bangor, ME (US)

(73) Assignees: Los Alamos National Security, LLC, Los Alamos, NM (US); University of Maine System Board of Trustees, Bangor, ME (US)

( * ) Notice: Subject to any disclaimer, the term of this patent is extended or adjusted under 35 U.S.C. 154(b) by 0 days.

(21) Appl. No.: 14/454,849

(22) Filed: Aug. 8, 2014

(65) Prior Publication Data

US 2015/0051072 A1 Feb. 19, 2015

Related U.S. Application Data

(60) Provisional application No. 61/866,681, filed on Aug. 16, 2013.

(51) Int. Cl.
| | | |
|---|---|---|
| A01N 25/00 | (2006.01) |
| A01N 33/02 | (2006.01) |
| A01N 43/40 | (2006.01) |
| A01N 43/48 | (2006.01) |
| C05G 3/00 | (2006.01) |
| A01N 43/36 | (2006.01) |
| A01N 43/62 | (2006.01) |
| A01N 37/42 | (2006.01) |
| A01N 43/44 | (2006.01) |
| C05F 11/00 | (2006.01) |

(52) U.S. Cl.
CPC .......... *C05G 3/00* (2013.01); *A01N 25/00* (2013.01); *A01N 37/42* (2013.01); *A01N 43/36* (2013.01); *A01N 43/40* (2013.01); *A01N 43/44* (2013.01); *A01N 43/62* (2013.01); *C05F 11/00* (2013.01)

(58) Field of Classification Search
None
See application file for complete search history.

(56) References Cited

U.S. PATENT DOCUMENTS

| | | |
|---|---|---|
| 2007/0105719 A1 | 5/2007 | Unkefer |
| 2012/0090365 A1 | 4/2012 | Ersek et al. |
| 2014/0275624 A1 | 9/2014 | Unkefer et al. |

OTHER PUBLICATIONS

Chanh Ta et al, "Utilization of the Amide Groups of Asparagine and 2-Hydroxysuccinamic Acid by Young Pea Leaves", Plant Physiol., Jan. 1984, 75, 527-530.
Meister, "Preparation And Enzymatic Reactions Of The Keto Analogues Of Asparagine And Glutamine", J. Biol. Chem., Aug. 1953, 571-589.
Stephani, R. and Meister, A., "Structure Of The Dimeric aXeto Acid Analogue of Asparagine" The Journal Of Biological Chemistry, 246(23), Dec. 10, 1971, 7115-7118.
Weygand, "Synthese von 1.5-Diaza~-cyclooctan-dion(4.8)-dicarbonsaure-(2.6)", Feb. 2, 1954, 482-488—with English Abstract.
International Patent Application No. PCT/US2014/050274: International Search Report and Written Opinion dated Nov. 18, 2014, 12 pages.
Ta et al, "Utilization of the Amide Groups of Asparagine and 2-hydroxysuccinamic Acid by Young Pea Leaves", Plant Physiol, 1984, 75, 527-530.

*Primary Examiner* — Alton Pryor
(74) *Attorney, Agent, or Firm* — Baker & Hostetler LLP (57) ABSTRACT

The invention is directed to methods and compositions for increasing a growth characteristic of a plant, increasing nutrient use efficiency of a plant, or improving a plant's ability to overcome stress comprising applying a composition comprising ketosuccinamate, a derivative thereof, or a salt thereof, to the plant or to a propagation material of the plant.

36 Claims, 1 Drawing Sheet

COMPOUNDS AND METHODS FOR IMPROVING PLANT PERFORMANCE

CROSS REFERENCE TO RELATED APPLICATIONS

This application claims the benefit of U.S. Provisional Application No. 61/866,681, filed Aug. 16, 2013, the entirety of which in incorporated herein by reference.

GOVERNMENT RIGHTS

This invention was made with government support under Contract No. DE-AC52-06NA25396 awarded by the U.S. Department of Energy. The government has certain rights in the invention.

TECHNICAL FIELD

The invention is directed to compositions and methods for improving growth characteristics of a plant, increasing nutrient use efficiency of a plant, or improving a plant's ability to overcome stress.

BACKGROUND

As the human population increases worldwide and available farmland continues to be destroyed or otherwise compromised, the need for more effective and sustainable agriculture systems is becoming of paramount interest to the human race. Improving biomass production, crop yields, protein content, plant growth rates, etc. represent major objectives in the development of agriculture systems that can more effectively respond to environmental and economic challenges.

Nitrogen is considered a critical growth-limiting element in plant growth and production. It is a key component of chlorophyll and amino acids and is found in adenosine triphosphate (ATP) and nucleic acids. Plants acquire nitrogen from the atmosphere in the form of $N_2$ gas and/or from the soil (e.g., fertilizer and decomposition of organic matter) but can only use the element in a reduced form (e.g., $NH_3$). The conversion of atmospheric nitrogen ($N_2$) to ammonia ($NH_3$) is "nitrogen fixation" and is carried out via the enzyme "nitrogenase" by a specialized group of prokaryotes that have a symbiotic relationship with the plant. Plants can readily assimilate $NH_3$ and use the molecule as the basis for producing key biological components (e.g., chlorophyll and amino acids) that promote growth and production in the plant.

Unfortunately, nitrogen fixation is a limiting step for plants to acquire $NH_3$, and as a result, modern day agriculture has supplemented with industrially-produced nitrogen fertilizers. That widespread fertilizer use has led to worldwide ecological problems such as the formation of coastal dead zones (due primarily to run-off into streams and oceans), which have a dramatic impact to the marine wildlife.

As a result, there continues to be a need for improved, cost-effective, and ecologically sound compositions and methods to improve plant growth, biomass production, grain yield, etc.

SUMMARY

The invention is directed to methods for increasing a growth characteristic of a plant, increasing nutrient use efficiency of a plant, or improving a plant's ability to overcome stress comprising applying a composition comprising ketosuccinamate, a derivative thereof, or a salt thereof, to the plant or to a propagation material of the plant. The invention is also directed to compositions comprising ketosuccinamate, or a derivative thereof, or a salt thereof; a carrier; and optionally, a plant growth stimulating compound.

BRIEF DESCRIPTION OF THE DRAWINGS

FIG. 1 depicts a metabolic diagram of nitrogen assimilation in plants as understood in the art. Nitrogen assimilation and primary metabolism (solid lines) begin with the formation of glutamine by the glutamine synthetase (GS)-catalyzed combination of glutamate and ammonia. One nitrogen from glutamine is then donated to 2-oxoglutarate to form glutamate. Aspartate and asparagine are formed from the oxaloacetate carbon backbone and one nitrogen from glutamate and another from glutamine. 2-Oxoglutaramate and ketosuccinamate are formed form glutamine and asparagine, respectively (dashed lines).

DETAILED DESCRIPTION OF ILLUSTRATIVE EMBODIMENTS

Figure 1:
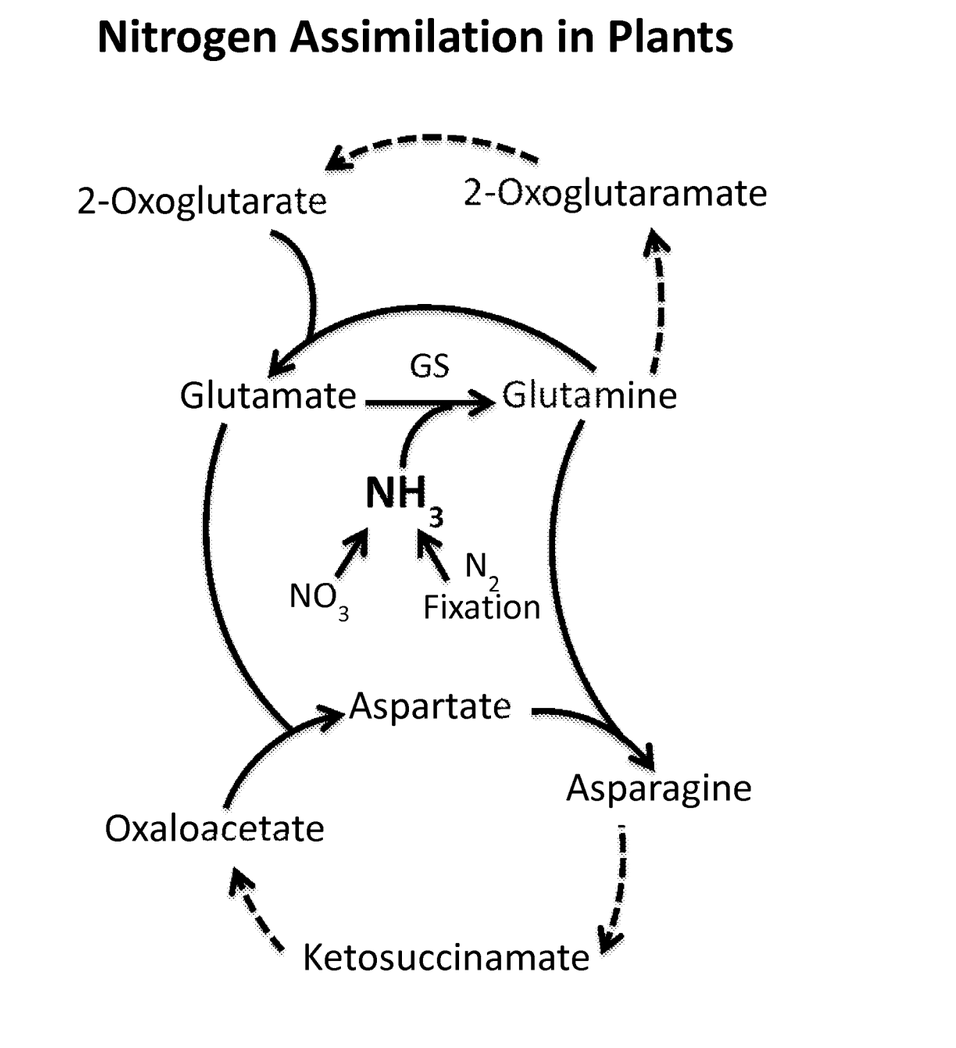

The present invention removes or minimizes the present ecological and cost disadvantages of industrial nitrogen supplementation for crops by maximizing plants' abilities to utilize available nitrogen, thus reducing the amount of supplementation required. The present invention is directed to methods of improving certain aspects of plant performance by applying a composition comprising ketosuccinamate, or a salt thereof, to the plant or to a propagation material of the plant. Derivatives of ketosuccinamate, or salts thereof, can also be used in the methods of the invention.

Ketosuccinamate, also known in the art as 2-oxosuccinamate, L-oxosuccinamate, alpha-ketosuccinamate, 3-carbamoyl-2-oxopropanoate, and 4-amino-2,4-dioxobutanoate, has the following structure:

Ketosuccinamate can also exist in the form of a dimer, which is also within the scope of the invention. Ralph A Stephani and Alton Meister 1971 "Structure of the dimeric a-ketoanalogue of asparagine" J. Biol Chem. 246:7115-7118. "Derivatives of ketosuccinamate," as used herein, refers to chemical compounds that are derived from ketosuccinamate by a chemical or physical process. The derivative may be a structural and/or functional analog. Derivatives of ketosuccinamate include, for example, compounds set forth in Table 1.

TABLE 1

| Ketosuccinamate Derivative | Chemical Structure |
|---|---|
| Dimeric structure of ketosuccinamte | ![structure] |

TABLE 1-continued

| Ketosuccinamate Derivative | Chemical Structure |
|---|---|
| Ketosuccinamate (4-amino-2,4-dioxobutanoic acid) | |
| (S)-4-oxo-2-azetidinecarboxylic acid (CAS # 16404-94-7) | |
| (R)-4-oxo-2-azetidinecarboxylic acid (CAS # 62860-12-2) | |
| 4,8-dioxo-1,5-diazocane-2,6-dicarboxylic acid | |
| 2,6-dihydroxy-4,8-dioxo-1,5-diazocane-2,6-dicarboxylic acid | |

Ketosuccinamate, as well as derivatives thereof, may be purchased or synthesized as described herein or via means known to those of ordinary skill in the art. See, for example, Meister A., J. Biol. Chem., (1953) 200:571-589; Weygand, Freidrich and Heinz-Jurgen Dietrich 1954 Synthese von 1.5-diaza-cyclooctan-dion-(4.8)-dicarbonsaure-(2.6) Chemische Berichte 87(4): 482-488.

The compositions of the invention can be applied using any of the methods known in the art, such as, for example, spraying, irrigating, coating, emersion, injecting, or any combination thereof.

Methods of the present invention include increasing a growth characteristic of a plant comprising applying a composition comprising ketosuccinamate, or a derivative thereof, or a salt thereof, to the plant or to a propagation material of the plant. Those skilled in the art understand that "growth characterics" include, for example, biomass, foliar tissue weight, nodulation number, nodulation mass, nodulation activity, number of seed heads, number of tillers, number of flowers, number of tubers, tuber mass, bulb mass, oil content, number of seeds, total seed mass, average seed mass, rate of leaf emergence, root mass, total below ground tissue weight, harvestable fruit or nut yield, plant protein and starch content, rate of biomass accumulation, rate of tiller emergence, rate of tiller growth, average fruit weight, germination rate, seedling emergence rate, or any combination thereof. In exemplary embodiments of the invention, the methods will result in an increase in biomass, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, or any combination thereof. By using the compositions and methods of the invention, the growth characteristic of a plant will be increased as compared to a plant growth in the absence of the compositions and methods of the invention.

Other embodiments of the invention are directed to methods of increasing nutrient use efficiency of a plant comprising applying a composition comprising ketosuccinamate, or a derivative thereof, or a salt thereof, to the plant or to a propagation material of the plant. "Nitrogen use efficiency (NUE)," as used herein, refers to a measure of crop production per unit of nitrogen fertilizer input. For most agricultural systems, over 50% and up to 75% of the nitrogen applied to the field is not used by the plant, and is lost to leaching into the soil or to runoff into surface waters. Increasing NUE, therefore, increases efficiency.

NUE may be measured by methods known to one of ordinary skill in the art. One measure of crop production related to NUE is fertilizer nitrogen use efficiency. Another measure of crop production related to NUE is total nitrogen use efficiency. Other measures of NUE include different measures of yield. For example, NUE may refer to increased protein content or concentration in leaves, grains or other plant tissues or organs. NUE can also refer to increased amino acid content or concentration in leaves, grains, or other plant tissues or organs. A combination of increased protein and amino acid content or concentration in leaves, grains, or other plant tissues or organs is also a measure of NUE.

Still other embodiments of the invention are directed to methods of improving a plant's ability to overcome stress comprising applying a composition comprising ketosuccinamate, or a derivative thereof, or a salt thereof, to the plant or to a propagation material of the plant. "Stress," as used herein, refers to any undesirable external factor. For example, the methods of the invention increase a plant's ability to overcome biotic stress. "Biotic stress" is a stress that occurs as a result of damage done to a plant by other living organisms, for example, insects, viruses, fungi, parasites, weeks, and animals. The methods of the invention also increase a plant's ability to overcome abiotic stress. "Abiotic stress" is a stress that occurs as a result of non-living factors, for example, sun, wind, fire, flood, and drought. The methods of the invention also increase a plant's ability to overcome chemical stress, such as that due to pesticides, fungicides, herbicides, anti-bacterials, or anti-viral compositions.

Plants that can benefit from the methods described herein include monocotyledon plants and dicotyledon plants. These include, but are not limited to, grains, legumes, fiber producing plants, oil producing plants, tuber producing plants, starch producing plants, grasses, vines, fruits, vegetables, flowering plants, and trees. Particular types of plants within the scope of the invention include, for example, wheat, oat, rice, corn, bean, soybean, barley, cotton, canola, flax, legume, grape, berry, tomato, vine, orange, nut, tobacco, alfalfa, potato, peanut, and *Arabidopsis*.

The compositions of the invention can be applied pre-emergent (before the seedlings emerge or appear above ground) or post-emergent (after the seedlings emerge or appear above ground) of the plant. The compositions of the invention can be applied directly to the plant or part of the plant, for example, a leaf, a root, a foliar, foliage, a tiller, a flower, a plant cell, a plant tissue, or a combination thereof. The compositions of the invention can also be applied to the growth medium.

The compositions of the invention can also be applied to a propagation material of the plant. For example, the compositions of the invention can be applied to a seed, a grain, a fruit, a tuber, a rhizome, a spore, a cutting, a slip, a meristem tissue, a plant cell, nut, or an embryo.

The compositions of the invention include ketosuccinamate, or a derivative thereof, or salt thereof and a carrier such as those routinely used in the art. The compositions can be an aqueous solution, a non-aqueous solution, a suspension, a gel, a foam, a paste, a powder, a dust, a solid, or an emulsion. Particularly preferred are aqueous formulations.

The concentration of the ketosuccinamate, or a derivative thereof, or salt thereof, will be the concentration necessary to achieve the desired effect, which can be elucidated by the person skilled in the art without undue experimentation. For example, compositions of the invention can include ketosuccinamate, or a derivative thereof, or salt thereof at a concentration of about 0.1 µM to about 10 mM. In preferred embodiments, the concentration is from about 0.1 mM to about 10 mM. In other embodiments, the concentration is from about 0.1 µM to about 2000 µM. In yet other embodiments, the concentration is from about 1 µM to about 250 µM.

In addition to the ketosuccinamate, or a derivative thereof, or salt thereof, compositions of the invention can optionally include at least one other plant growth stimulating compound. The ketosuccinamate, or a derivative thereof, or salt thereof, can be present in any ratio with the other plant growth stimulating compound. For example, the ratio of ketosuccinamate, or a derivative thereof, or salt thereof to the other plant growth stimulating compound(s) can be in the range of 99:1 to 1:99. In other embodiments, the ratio is 90:10. In still other embodiments, the ratio is 80:20. In yet other embodiments, the ratio is 70:30. In further embodiments, the ratio is 60:40. In still other embodiments, the ratio is 50:50. In additional embodiments, the ratio is 40:60. In still other embodiments, the ratio is 30:70. In other embodiments, the ratio is 20:80. In yet other embodiments, the ratio is 10:90.

Such other growth stimulating compounds are known in the art, per se. Particularly preferred plant growth stimulating compounds for use in the compositions of the invention include, for example, (R)-2-hydroxy-5-oxopyrrolidine-2-carboxylic acid, (S)-5-oxopyrrolidine-2-carboxylic acid, and combinations thereof. See, for example, U.S. Published Application No. 2007/0105719.

(R)-2-hydroxy-5-oxopyrrolidine-2-carboxylic acid (S)-5-oxopyrrolidine-2-carboxylic acid Compositions of the invention can also further include additional components routinely used in the art, for example, humectants, adjuvants, antioxidants, stabilizers, plant macronutrients, plant micronutrients, pesticides, fungicides, antivirals, anti-bacterials, herbicides, and combinations thereof.

Compositions of the invention can also further include microbes, for example nitrogen fixing microbes or microrrhizae.

Compositions of the invention can also further include plant propagation materials, for example, seeds, grains, spores, and the like.

The treatment of the plants, their propagation material, and/or growth substrates can be accomplished, for example, in such a way that the plant, a part thereof, its propagation material and/or its growth substrate is treated with a ketosuccinamate, a derivative thereof, or salt thereof, and optionally, another plant growth stimulating compound. The plant, its propagation material, and/or its growth substrate can be treated once or more than once. For example, in treatment regimes that include treating more than one time, the time interval between the treatments must be such that the desired effect can take place. The time interval may be second(s); minute(s); hour(s); day(s), week(s), and month(s).

Alternatively, the plant, its propagation material, and/or its growth substrate can be treated with ketosuccinamate, or a derivative thereof, or salt thereof, and another plant growth stimulating compound in separate form, it being possible for the treatment with the individual active compounds to be accomplished simultaneously or in succession. In the case of successive treatment, the time interval between the treatments must be such that the desired effect can take place. The time interval may be second(s); minute(s); hour(s); day(s), week(s), and month(s).

For any treatment scenario described herein, it is possible to apply the compounds to different subjects (subjects being, in the present context, plant, propagation material, and growth substrate), that is, for example, to treat the seed with ketosuccinamate, or a derivative thereof, or salt thereof, and to apply the plant growth stimulating compound, to the plant which develops from the seed and/or to treat their growth substrate therewith. Alternatively, to treat the seed with the plant growth stimulating compound, and to apply ketosuccinamate, or a derivative thereof, or salt thereof, to the plant which develops from the seed and/or to treat their growth substrate therewith. A combination of the two approaches described above may also be pursued.

In another treatment scenario, the seed may be treated with ketosuccinamate, or a derivative thereof, or salt thereof in combination micronutrients, macronutrients, other plant growth characteristic promoting compounds, pesticides and/or herbicides.

In another treatment scenario, the seed may be treated before sowing or else via the growth substrate into which it is sown, for example during sowing in the form of what is known as the in-furrow application. In this form of application, ketosuccinamate, or a derivative thereof, or salt thereof and/or the other plant growth stimulating compound are placed into the furrow essentially at the same time as the seed.

A range of treatment ratios may also be pursued. For example, the ratio of ketosuccinamate compound to plant growth stimulating compound may range from 99:1 to 1:99 (or 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:35, 64:36, 63:37, 62:38, 61:39, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:93, 4:96, 3:97, 2:98 or 1:99). The ratio may apply to molar concentration ratios or weight ratios.

The ketosuccinamate, or a derivative thereof, or salt thereof, and/or the plant growth stimulating compound may be formulated, in the ready-to-use preparations, in suspended, emulsified or dissolved form, either jointly or separately. The use forms depend entirely on the intended purposes.

The ketosuccinamate, or a derivative thereof, or salt thereof, and/or the plant growth stimulating compound may be employed as such, in the form of their formulations or the use forms prepared therefrom, for example in the form of directly sprayable solutions, foams, powders, suspensions, or dispersions, also highly concentrated aqueous, oily or other suspensions or dispersions, emulsions, oil dispersions, pastes, dusts, tracking powders or granules. The application is usually accomplished by spraying, misting, atomizing, scattering or pouring. The use forms and use methods depend on the in-tended purposes.

Depending on the presentation in which the ready-to-use preparations of ketosuccinamate, or a derivative thereof, or salt thereof and/or the plant growth stimulating compound are present, they comprise one or more liquid or solid carriers, optionally surface-active substances and optionally further adjuvants which are conventionally used for the formulation of plant treatments. The compositions for such formulations are well known to one of ordinary skill in the art.

Aqueous use forms can be prepared for example starting from emulsion concentrates, suspensions, pastes, wettable powders or water-dispersible granules by adding water. To prepare emulsions, pastes, or oil dispersions, ketosuccinamate, or a derivative thereof, or salt thereof of and/or the plant growth stimulating compound, as such or dissolved in an oil or solvent, can be homogenized in water by means of wetter, adhesive, dispersant or emulsifier. However, it is also possible to prepare concentrates consisting of ketosuccinamate, or a derivative thereof, or salt thereof and/or the plant growth stimulating compound, wetter, adhesive, dispersant or emulsifier and, if appropriate, solvent or oil, and such concentrates are suitable for dilution with water.

The concentrations of ketosuccinamate, or a derivative thereof, or salt thereof and/or the plant growth stimulating compound in the ready-to-use preparations can be varied within substantial ranges. In general, they are between 0.0001 and 10%, preferably between 0.01 and 1% (% by weight total ketosuccinamate, or a derivative thereof, or salt thereof and/or the plant growth stimulating compound content based on the total weight of the ready-to-use preparation).

It is possible to add, to ketosuccinamate, or a derivative thereof, or salt thereof and/or the plant growth stimulating compound, oils of various types, wetters, adjuvants, herbicides, fungicides and insecticides which are other than ketosuccinamate, or a derivative thereof, or salt thereof and/or the plant growth stimulating compound employed in accordance with the invention, nematicides, other pesticides such as bactericides, fertilizers and/or growth regulators, if appropriate only just before use. These can be admixed to ketosuccinamate, or a derivative thereof, or salt thereof and/or the plant growth stimulating compound employed in accordance with the invention in a ratio of 99:1 to 1:99 (or 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34, 65:35, 64:36, 63:37, 62:38, 61:39, 60:40, 59:41, 58:42, 57:43, 56:44, 55:45, 54:46, 53:47, 52:48, 51:49, 50:50, 49:51, 48:52, 47:53, 46:54, 45:55, 44:56, 43:57, 42:58, 41:59, 40:60, 39:61, 38:62, 37:63, 36:64, 35:65, 34:66, 33:67, 32:68, 31:69, 30:70, 29:71, 28:72, 27:73, 26:74, 25:75, 24:76, 23:77, 22:78, 21:79, 20:80, 19:81, 18:82, 17:83, 16:84, 15:85, 14:86, 13:87, 12:88, 11:89, 10:90, 9:91, 8:92, 7:93, 6:94, 5:93, 4:96, 3:97, 2:98 or 1:99). The ratio may apply to molar concentration ratios or weight ratios.

It is possible to add, to ketosuccinamate, or a derivative thereof, or salt thereof and/or the plant growth stimulating compound, oils of various types, wetters, adjuvants, herbicides, fungicides and insecticides which are other than ketosuccinamate, or a derivative thereof, or salt thereof and/or the plant growth stimulating compound employed in accordance with the invention, nematicides, other pesticides such as bactericides, fertilizers and/or growth regulators. In one aspect, ketosuccinamate, or a derivative thereof, or salt thereof and/or the plant growth stimulating compound, may be combined with a nematicides, other pesticides such as bactericides, fertilizers and/or growth regulators prior to applying the combination to a plant or plant propagation material.

The formulations are prepared in a known manner, e.g. by extending ketosuccinamate, or a derivative thereof, or salt thereof thereof and/or the plant growth stimulating compound with solvents and/or carriers, if desired using surface-active substances, i.e. emulsifiers and dispersants. Solvents/auxiliaries which are suitable are essentially: water, aromatic solvents (for example Solvesso products, xylene), paraffins (for example mineral fractions), alcohols (for example methanol, butanol, pentanol, benzyl alcohol), ketones (for example cyclohexanone, methyl hydroxybutyl ketone, diacetone alcohol, mesityl oxide, isophorone), lactones (for example gamma-butyrolacton), pyrrolidones (pyrrolidone, N-methylpyrrolidone, N-ethylpyrrolidone, n-octylpyrrolidone), acetates (glycol diacetate), glycols, glycerol, fatty acid dimethylamides, fatty acids and fatty acid esters. In principle, solvent mixtures may also be used.

Carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of ligno-sulfonic acid, naphthalenesulfonic acid, phenolsulfonic acid, dibutylnaphthalenesulfonic acid, alkylarylsulfonates, SDS, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl poly-glycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol, polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, etha-nol, propanol, butanol, cyclohexanol, cyclohexanone, mesityl oxide, isophorone, strongly polar solvents, for example dimethyl sulfoxide, 2-pyrrolidone, N-methylpyrrolidone, butyrolactone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica, gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

Formulations for the treatment of seed may additionally comprise binders and/or gelling agents and, if appropriate, colorants.

In general, the formulations comprise from 0.01 to 95% by weight, preferably from 0.1 to 90% by weight, in particular from 5 to 50% by weight, of the active substance. The active substances are employed in a purity of from 90% to 100%, preferably 95% to 100% (according to NMR spectrum).

For the treatment of seed, the relevant formulations will give ketosuccinamate, or a derivative thereof, or salt thereof, and/or the plant growth stimulating compound concentrations of from 0.001% to 80% (or 0.001%, 0.005%, 0.01%, 0.02%, 0.03%, 0.04%, 0.05%, 0.06%, 0.07%, 0. by weight, preferably 0.1 to 40% by weight, in the ready-to-use preparations.

"Growth substrate," also refers to as "growth medium," as used herein, refers to any type of substrate in which the plant grows or will grow, such as soil (for example in a pot, in borders or in the field), water, or artificial media and any additional supplements whether related to growth (e.g., fertilizer) or protecting the plant (e.g., pesticide).

"NPKS Macronutrient" or "macronutrient," as used herein, refers to nutrients of nitrogen (N), phosphorus (P), potassium (K) and sulfur (S).

Micronutrient, as used herein, refers to any nutrient that is required for plant growth and/or reproduction.

"Nitrogen fixing bacterium," as used herein, refers to bacterium having the capability to fix or reduce nitrogen ($N_2$) from the atmosphere to form ammonia ($NH_3$).

"Nitrogen use efficiency (NUE)," as used herein, refers to a measure of crop production per unit of nitrogen fertilizer input. NUE may be measured by multiple different methods by one of ordinary skill in the art. Further, NUE may refer to fertilizer nitrogen use efficiency or to total nitrogen use efficiency. It may also include different measures of yield. For example, it may be used to refer to increased nitrogenous compounds in the plant such as increased protein content or concentration in leaves, grains or other plant tissues or organs. For most agricultural systems, over 50% and up to 75% of the nitrogen applied to the field is not used by the plant, and is lost to leaching into the soil or to runoff into surface waters.

"Nodulation," as used herein, refers to nodule weight, number of nodules and rate of nodule growth.

"Plant growth stimulating compound," as used herein, refers to a compound capable of improving plant performance or increasing a growth characteristic of a plant when the plant and/or plant propagation material is treated with an effective amount of the compound.

"Plant performance," as used herein, refers to a measure of one or more of the following characteristics: number of tillers, foliar biomass (weight), and seed heads. Plant performance improvement may be concluded when anyone of the above characteristics increases for a plant. For example, it is widely accepted by those skill in the art that increasing the number of tillers in a crop increases the seed yield. Further, increasing the amount or rate of foliar biomass indicates the size and rate of plant growth.

"Propagation material," as used herein, refers to material from which a complete plant can be grown. Non-limiting examples of propagation material includes seeds, grains, fruits, tubers, the rhizome, spores, cuttings, slips, meristem tissue, individual plant cells and any form of plant tissue from which a complete plant can be grown.

"Salts," as used herein, refers to ionic forms of any of the compounds of the invention in combination with any suitable counterion. The salts should be soluble or suspendible in the compositions of the invention. For example, salts of the compounds of the invention can be formed from anions of the described compounds with metal cations such as alkali metal cations (lithium, sodium, potassium, cesium, and rubidium), alkaline earth metal cations (magnesium, calcium, strontium, barium, and the like), and heavy metal cations (copper, silver, mercury, zinc, cadmium, chromium, manganese, iron, cobalt, nickel, aluminum, tin, and lead). Salts of the describe compounds can also be formed from onium cations, for example ammonium cations, sulfonium cations, sufoxonium cations, and phosphonium cations. Salts of the compounds of the invention can also be formed from cations of the described compounds with anions such as chloride, bromide, and the like.

"Symbiotic bacterium," as used herein, refers to nitrogen fixing bacteria that enter into a relationship with their specific host plant (legume plant). Non-limiting examples include the symbiosis between *Bradyrhizobium japonicum* and its host *Glycine max* (soybean), and *Sinorhizobium meliloti* and its host, *Medicago sativa* (alfalfa). In these relationships, each member of the association benefits from the presence of the other; the plant receives fixed nitrogen from the bacterium and the bacterial symbiont receives carbon skeletons from the plant. These associations reside in specialized root structures termed nodules that begin to form when the relationship is initiated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g., "or") should be understood to mean either one, both, or any combination thereof of the alternatives.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Unless otherwise noted, technical terms are used throughout this specification are according to conventional usage unless otherwise states. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

EXAMPLES

Example 1

Synthesis of 4-Amino-2,4-Dioxobutonic Acid

See e.g., Meister A., J. Biol. Chem., (1953) 200:571-589.

Example 2

Treatment of Wheat Plants

This example shows that treatment of wheat plants with ketosucinamate, alone or in combination with another plant growth stimulating compound, increases biomass, tiller lengths and seed heads, which is generally referred to as improving plants performance or increasing a growth characteristic of a plant.

The control group and treatment groups used Glenn, a spring wheat variety. The control group and each of the treatment groups consisted of 15 plants.

The control formulation was a base aqueous solution having a surfactant (sodium dodecylsulfate at 700 mg/L; SDS) and humectant (glycerol at 2 ml/L) at pH 7 (hereinafter "Base Solution").

The treatment formulations contained the Base Solution along with ketosuccinamate (Treatment Formulation #1), base solution with L-pyroglutamate (Treatment Formulation #2) or ketosuccinamate and L-pyroglutumate (Treatment Formulation #3; a 60:40 ratio of L-pyroglutamate:ketosuccinamate). These formulations are summarized in Table 2 below.

TABLE 2

| Group | Ketosuccinamate Concentration | L-Pyroglutamate Concentration |
|---|---|---|
| Control Formulation | 0 µM | 0 µM |
| Treatment Formulation #1 | 100 µM | 0 µM |
| Treatment Formulation #2 | 0 µM | 100 µM |
| Treatment Formulation #3 | 40 µM | 60 µM |

The spring wheat was planted on day 1 and grown in a greenhouse with natural day lengths. All plants were fed a commercially available complete nutrient mix (Flora Gro Bloom; GenHydro), which provided $NO_3$ and $NH_4$ as the nitrogen source in a ratio of 10:1. Each group was treated daily, starting on Day 10, via foliar spray, with their respective formulations.

Approximately 70 days after planting, the number of tillers was counted for the control group and the Treatment Formulation #1 group (ketosuccinamate compound alone). The number of tillers/group (15 plants) is shown in Table 3 below.

TABLE 3

| Group | Number of tillers per group of 15 plants |
|---|---|
| Control Formulation | 127 |
| Treatment Formulation #1 | 145 |

The data in Table 4 shows that the plants treated with ketosuccinamate (Treatment Formulation #1) had an increased number tillers compared to the number of tillers for the control group.

The plants were harvested on Day 91 and foliar tissue weight (in grams) and the number of seed heads/plant were measured. Table 4 below summarizes the measurements taken.

TABLE 4

| Group | Folia Tissue Fresh Weight | Number of Seed Heads Per Plant |
|---|---|---|
| Control Formulation | 11.0 g | 4.3 |
| Treatment Formulation #1 | 12.6 g | 4.6 |
| Treatment Formulation #2 | 13.3 g | 6.3 |
| Treatment Formulation #3 | 13.2 g | 5.3 |

The data in Table 5 shows that plants treated with ketosuccinmate alone (Treatment Formulation #1), L-pyroglutamate alone (Treatment Formulation #2) and the 60:40 ratio of L-pryoglutamate:ketosuccinamate (Treatment Formulation #3) had increased foliar tissue weight compared to the control group, and an increased number of seed heads/plant compared to the control group.

Example 3

Treatment of Soybean Plants

This example shows that treatment of soybean plants with ketosuccinamate increases foliar and nodule biomass generally referred to as improving plants performance.

The control group and treatment groups used a commercially available variety of soybean. The control group and the treatment groups each consisted of 15 plants. The control formulation was the Base Solution (see Example 2). The treatment formulation contained the Base Solution along with ketosuccinamate (Treatment Formulation #1). These formulations are summarized in the Table 5 below.

TABLE 5

| Group | Ketosuccinamate Concentration |
|---|---|
| Control Formulation | 0 μM |
| Treatment Formulation #1 | 100 μM |

The soybean plants were grown in a greenhouse with natural day lengths. The growth substrate was peat moss (moist), horticulture vermiculate (moist), and sand in equal volumes. The percent soil moisture was maintained from about 20% to about 30% saturation. All plants were fed weekly a commercially available complete nutrient mix (Flora Gro) with KCl substituted for the nitrogen, and $CoCl_2$ added to provide for this trace element. NDURE® inoculant was mixed into the substrate before the soybeans were planted. Each group was treated daily via foliar spray 10 days after planting/inoculation with their respective formulations.

The plants were harvested 91 days after planting and foliar tissue weight (in grams) and nodule weight (mg)/plant were measured. Table 6 below summarizes the measurements taken.

TABLE 6

| GROUP | Foliar Tissue Fresh Weight | Nodules Per Plant |
|---|---|---|
| Control Formulation | 2.1 g | 24.8 mg |
| Treatment Formulation #1 | 2.6 g | 85.6 mg |

The data in Table 7 shows that plants treated with ketosuccinmate alone (Treatment Formulation #1) had increased foliar tissue weight compared to the control group, and an increased nodules weight/plant compared to the control group.

Example 4

Treatment of Alfalfa Plants

This example shows that treatment of alfalfa plants with ketosuccinamate, alone or in combination with another plant growth stimulating compound (e.g., L-pyroglutamate), increases biomass, generally referred to as improving plants performance.

The control group and treatment groups used Ladak variety of alfalfa. The control group and each of the treatment groups consisted of 15 plants. The control formulation was the Base Solution. See Example 2. The treatment formulations contained the Base Solution along with ketosuccinamate (Treatment Formulation #1), base solution with L-pyroglutamate (Treatment Formulation #2) or ketosuccinamate and L-pyroglutumate (Treatment Formulation #3; a 50:50 ratio of L-pyroglutamate:ketosuccinamate). These formulations are summarized in the Table 7 below.

TABLE 7

| Group | Ketosuccinamate Concentration | L-Pyroglutamate Concentration |
|---|---|---|
| Control Formulation | 0 μM | 0 μM |
| Treatment Formulation #1 | 100 μM | 0 μM |

TABLE 7-continued

| Group | Ketosuccinamate Concentration | L-Pyroglutamate Concentration |
|---|---|---|
| Treatment Formulation #2 | 0 μM | 100 μM |
| Treatment Formulation #3 | 50 μM | 50 μM |

The alfalfa plants were grown in a greenhouse with natural day lengths. All plants were fed nitrogen free media (Columbia without nitrogen). The growth substrate was peat moss (moist), horticulture vermiculate (moist), and sand in equal volumes. The percent soil moisture was maintained from about 20% to about 30% saturation. NDURE inoculant was mixed into the substrate before the alfalfa seeds were planted. Each group was treated daily via foliar spray 10 days after planting with their respective formulations. Treatments were every other day.

The plants were harvested 85 days after planting, and foliar tissue weight (in grams) was measured. Table 8 below summarizes the measurements taken.

TABLE 8

| Group | Foliar Tissue Fresh Weight |
|---|---|
| Control Formulation | 8.6 g |
| Treatment Formulation #1 | 9.2 g |
| Treatment Formulation #2 | 12.4 g |
| Treatment Formulation #3 | 14. g |

The data in Table 8 shows that plants treated with ketosuccinmate alone (Treatment Formulation #1), L-pyroglutamate alone (Treatment Formulation #2), and the 50:50 ratio of L-pryoglutamate:ketosuccinamate (Treatment Formulation #3) had increased foliar tissue weight compared to the control group.

Example 5

Measuring Plant Protein Content

Leaf protein is an indication of the nitrogen use efficiency in plants, the potential that the plant has to fully develop and maximize production of its seeds and fruits. It is also a measure of the nutritional value of the plant tissue. For example, the legume alfalfa foliar tissues are used as a forage to enrich the protein composition of an animal's diet. The leaf protein will be measured in plants treated according to the invention and compared with untreated control plants of the same species grown under the same conditions and provided the same composition and levels of nutrients.

The leaf samples will be taken from leaves in the same position in the canopy and will be at the same stage of development. They will be fully expanded leaves of at least one-third maximum leaf size for the species. The plants to be exampled will be at least one monocot plant such as wheat, rice, or barley and at least one dicot plant such as soybean, alfalfa, lettuce or peppers. The protein will be measured using the standard Bradford protein assay using the Bradford reagent according to the manufacturer's instructions. This reagent is based on the brilliant blue G dye and the protein dye complex that is formed is quantitatively related to the optical density at 595 nm.

Plants that are treated with ketosuccinamate, or a derivative thereof, or in combination with another nutrient or plant growth stimulating compound will have an increased growth plant characteristic (e.g., increased protein content) as compared to an untreated plant.

Example 6

Measuring Plant Amino Acid Content

The free amino acid pools in the leaves of plants treated according to the invention will be compared with those of untreated control plants of the same species and grown under the same growth conditions and provided the same composition and levels of nutrients. The amino acid pools will reflect the overall status of nitrogen metabolism in the plants.

The amino acid pool sizes will reflect the overall robustness of a plants metabolism and provide insight to the flux though certain amino acid biosynthesis pathways that are important for such important properties as safening from certain types of herbicides. In particular, any agent that improves amino acid biosynthesis will provide a measure of safening against the actions herbicides that target amino acid biosynthesis. Safening is highly desirable for the crop that is to be protected from the herbicide that is being used to reduce weeds in competition with the crop.

For herbicides that target acetolactate synthase (such as Osprey) any agent that will increase isoleucine and valine biosynthesis will provide safening. The same is true for herbicides that target aromatic amino acid biosynthesis such as glyphosate and any agent that increases aromatic amino acid biosynthesis would be expected to provide safening against these herbicides.

Any agent that stimulates glutamine synthesis will be expected to provide safening against herbicides containing glufosinate, a glutamine synthetase-targeting herbicide. These are marketed under names such as BASTA, RELY, FINALE and other names.

The growth of plants treated according to the invention and representatives of the amino acid biosynthesis-targeting herbicides will be compared with plants treated with only the herbicide. The ketosuccinamate will be tested using the standard effective dose and protocol; the herbicide will be used at levels ranging from less than to its full recommended lethal dose. The test doses will be between 10% and 100% of the recommended lethal dose. The growth of the plants will be characterized using standard methods that include final biomass (of either foliar regions or roots or whole plant) and tracking leaf, tiller or flower emergence. The plant species to be tested shall represent monocots (wheat, rice or barley) and dicots (soybean, cotton, peppers, lettuce or other vegetable)

It is expected that a plant that is treated, or a seed of a plant that is treated, or the soil where a plant is grown is treated, according to the invention will have an increased growth plant characteristic (e.g., increased and/or improved amino acid biosynthesis) compared to an untreated plant or untreated seed or untreated soil.

Example 7

Germination and Seedling Development

Method for Seed Treatment

The desired treatment concentration of ketosuccinamate was added to an aqueous solution of 0.01% Tween 80 and the pH was set to neutral with KOH. The seeds were dipped in the solution to wet them and allowed to air dry before planting, a process that required less than 15 min.

Germination

Alfalfa (variety Ladak) 3 days after initiation of germination on moist paper toweling at 65-75° F. the following percent germination was observed. Control untreated seeds: 80%, seeds treated with 0.1 mM ketosuccinamate: 88% and seeds treated with 1 mM ketosuccinamate: 93%. At least 30 seeds were used in each set.

Soybean (variety Viking) 22 hr after treatment and initiation of germination on moist paper toweling at 75-85° F. the following germination was observed. 2 of the 20 controls had broken through the pericarp whereas 9 of the 20 ketosuccinamate (10 mM) treated seeds had broken through the pericarp. 24 hours after treatment 6 of the 20 controls had broken the pericarp and 12 of the 20 ketosuccinamate-treated seeds had broken the pericarp.

Greenhouse Seedling Emergence

Soybeans (Variety Viking)

Seeds were planted in vermiculite, sand, peat moss (1:1:1) in the greenhouse and the seedling emergence was tracked. The moisture in the germination/growth substrate as maintained between 15-20% of saturation. The temperature in the house ranged from 72-82° F. *Bradyrhizobium japonicum* (commercial innoculum) was mixed into the substrate before planting.

3 days after planting the following seedling emergence was observed. Controls 12 of 20 had emerged from the soil. Ketosuccinamate (1 mM) treated 16 of 20 had emerged.

Alfalfa (Variety Ladak)

Seeds were planted in vermiculite, sand, peat moss (1:1:2) in the greenhouse and the seedling emergence was tracked. The temperature in the house ranged from 72-82° F. *Sinorhizobium meliloti* inoculum (commercial innoculum) was mixed into the substrate before planting.

3 days after planting, the following seedling emergence was observed. Control 58%; Ketosuccinamate (1 mM) treated 79%.

What is claimed:

1. A method for increasing a growth characteristic of a plant, increasing nutrient use efficiency of a plant, or improving a plant's ability to overcome stress comprising applying a composition comprising ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or a salt thereof, to the plant or to a propagation material of the plant.

2. The method of claim 1, wherein the composition is applied to a part of the plant that is a leaf, a root, a foliar, foliage, a tiller, a flower, a plant cell, a plant tissue, or a combination thereof.

3. The method of claim 1, wherein the propagation material of the plant is a seed, a grain, a fruit, a tuber, a rhizome, a spore, a cutting, a slip, a meristem tissue, a plant cell, nut, or an embryo.

4. The method of claim 1, wherein the application is pre-emergence or post-emergence.

5. The method of claim 1, wherein the growth characteristic is biomass, foliar tissue weight, nodulation number, nodulation mass, nodulation activity, number of seed heads, number of tillers, number of flowers, number of tubers, tuber mass, bulb mass, oil content, number of seeds, total seed mass, average seed mass, rate of leaf emergence, root mass, total below ground tissue weight, harvestable fruit or nut yield, plant protein and starch content, rate of biomass accumulation, rate of tiller emergence, rate of tiller growth, average fruit weight, germination rate, seedling emergence rate, or a combination thereof.

6. The method of claim 1, wherein the growth characteristic is biomass, foliar tissue weight, nodulation number, nodulation mass, nodulation activity, number of seed heads, number of tillers, number of flowers, number of tubers, tuber mass, bulb mass, number of seeds, total seed mass, rate of leaf emergence, rate of tiller emergence, rate of seedling emergence, or a combination thereof.

7. The method of claim 1, wherein the increased nutrient use efficiency is increased protein content, increased amino acid content, or a combination thereof.

8. The method of claim 1, wherein the stress is biotic, abiotic stress, or chemical stress, or herbicidal stress.

9. The method of claim 8, wherein the biotic stress is due to insects, viruses, fungi, parasites, weeds, or animals.

10. The method of claim 8, wherein the abiotic stress is due to sun, wind, fire, flood, or drought.

11. The method of claim 8, wherein the chemical stress is due to pesticide, fungicide, herbicide, anti-bacterial, or antiviral compositions.

12. The method of claim 1, wherein the composition is an aqueous solution, a non-aqueous solution, a suspension, a gel, a foam, a paste, a powder, a dust, a solid, or an emulsion.

13. The method of claim 12, wherein the composition is an aqueous formulation.

14. The method of claim 1, wherein the concentration of the ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof in the composition is from about 0.1 µM to about 10 mM.

15. The method of claim 14, wherein the concentration of the ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof in the composition is from about 0.1 mM to about 10 mM.

16. The method of claim 14, wherein the concentration of the ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof in the composition is from about 1 µM to about 250 µM.

17. The method of claim 1, wherein the composition further comprises a surfactant, a humectant, an adjuvant, an antioxidant, a stabilizer, a plant macronutrient, a plant micronutrient, a pesticide, a fungicide, an antiviral, an anti-bacterial, a herbicide, or a combination thereof.

18. The method of claim 1, wherein the composition further comprises a plant growth stimulating compound.

19. The method of claim 18, wherein the plant growth stimulating compound is (R)-2-hydroxy-5-oxopyrrolidine-2-carboxylic acid, (S)-5-oxopyrrolidine-2-carboxylic acid, or a combination thereof.

20. The method of claim 18, wherein the ratio of the ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof to the plant growth stimulating compound is from about 99:1 to about 1:99.

21. The method of claim 1, wherein the plant is a monocotyledon plant or a dicotyledon plant.

22. The method of claim 1, wherein the plant is a grain, legume, fiber producing plant, oil producing plant, tuber producing plant, starch producing plant, grass, vine, fruit, vegetable, flowering plant, or tree.

23. The method of claim 1, wherein the plant is wheat, oat, rice, corn, bean, soybean, barley, cotton, canola, flax, legume, grape, berry, tomato, vine, orange, nut, tobacco, alfalfa, potato, peanut, or *Arabidopsis*.

24. A composition to be applied to a plant or to a propagation material of a plant comprising
ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or a salt thereof; and
a carrier.

25. The composition of claim 24, wherein the formulation is an aqueous solution, a non-aqueous solution, a suspension, a gel, a foam, a paste, a powder, a dust, a solid, or an emulsion.

26. The composition of claim 24, wherein the concentration of ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof is from about 0.1 µM to about 10 mM.

27. The composition of claim 24, wherein the concentration of the ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof is from about 0.1 mM to about 10 mM.

28. The composition of claim 24, wherein the concentration of the ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof is from about 1 µM to about 250 µM.

29. The composition of claim 24, further comprising a surfactant, a humectant, an adjuvant, an antioxidant, a stabilizer, a plant macronutrient, a plant micronutrient, a pesticide, a fungicide, an antiviral, an anti-bacterial, a herbicide, or a combination thereof.

30. The composition of claim 24, further comprising a microbe.

31. The composition of claim 30, wherein the microbe is a nitrogen fixing microbe or a microrrhizae.

32. The composition of claim 24, further comprising a plant propagation material.

33. The composition of claim 24, further comprising a plant growth stimulating compound.

34. The composition of claim 33, wherein the ratio of the plant growth stimulating compound to ketosuccinamate, 3-carbamoyl-2,4-dihydroxy-6-oxopiperidine-2,4-dicarboxylate; (S)-4-oxo-2-azetidinecarboxylic acid; (R)-4-oxo-2-azetidinecarboxylic acid; 4,8-dioxo-1,5-diazocane-2,6-dicarboxylic acid; or 2,6-dihydroxy-4,8-dioxo-1,5-diazocane-2,6-dicarboxylic acid; or salt thereof is from about 99:1 to about 1:99.

35. The composition of claim 33, wherein the concentration of the plant growth stimulating compound is from about 0.1 µM to about 2000 µM.

36. The composition of claim 33, wherein the plant growth stimulating compounds is (R)-2-hydroxy-5-oxopyrrolidine-2-carboxylic acid, (S)-5-oxopyrrolidine-2-carboxylic acid, or a combination thereof.

* * * * *